United States Patent [19]

Busta et al.

[11] Patent Number: 5,137,817
[45] Date of Patent: Aug. 11, 1992

[54] APPARATUS AND METHOD FOR ELECTROPORATION

[75] Inventors: Heinz H. Busta, Park Ridge; Michael L. Bittner, Naperville; Richard E. Cuellar, Glen Ellyn, all of Ill.

[73] Assignee: Amoco Corporation, Chicago, Ill.

[21] Appl. No.: 593,033

[22] Filed: Oct. 5, 1990

[51] Int. Cl.⁵ ............... C12N 13/00; B01D 61/42; C25D 13/00
[52] U.S. Cl. ............... 435/173; 204/299 R
[58] Field of Search ............ 204/299 R, 180.1; 435/172.1, 172.2, 173

[56] References Cited

U.S. PATENT DOCUMENTS 4,822,470  4/1989  Chang ............... 204/299 R
4,923,814  5/1990  Marshall, III ............... 435/173

Primary Examiner—John F. Niebling
Assistant Examiner—Caroline Koestner
Attorney, Agent, or Firm—James A. Gabala; William H. Magidson; Frank J. Sroka

[57] ABSTRACT

An electrode set for electrotransformation of a host cell by electroporation, comprising: an electrically insulating substrate; and at least one pair of interdigitated electrodes which are carried by said substrate and which lie in a generally planar array, said electrodes and said substrate being adopted to carry a cell transformant and a host cell thereon, said electrodes and said host cell and said cell transformant being adapted to pass electrical current upon the application of a potential difference across said electrodes.

15 Claims, 5 Drawing Sheets

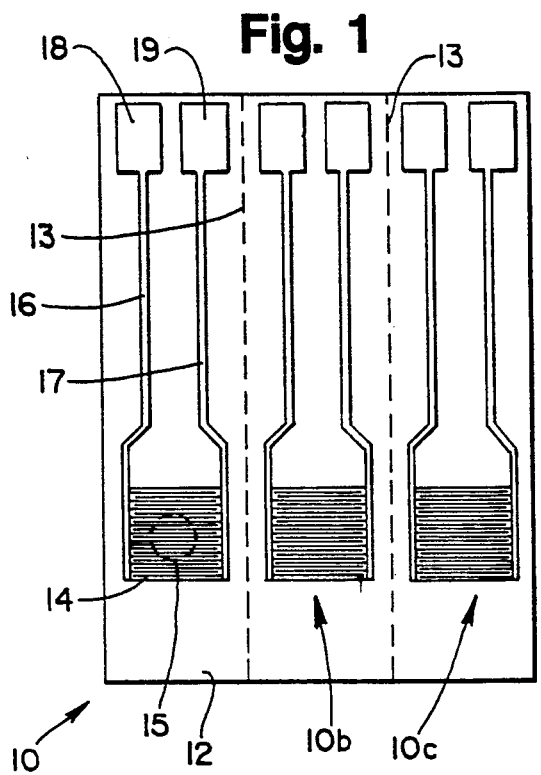
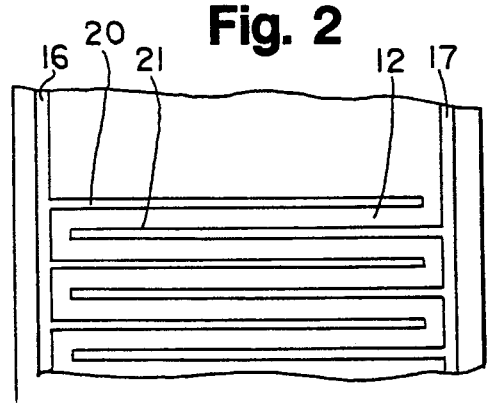
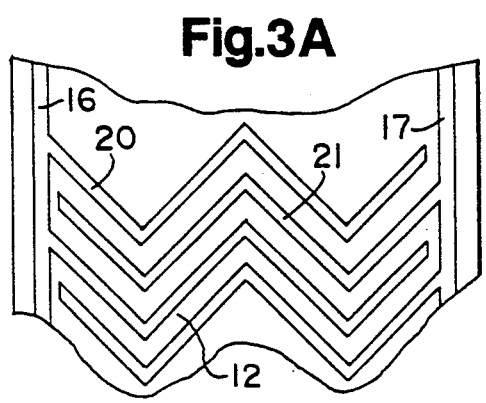
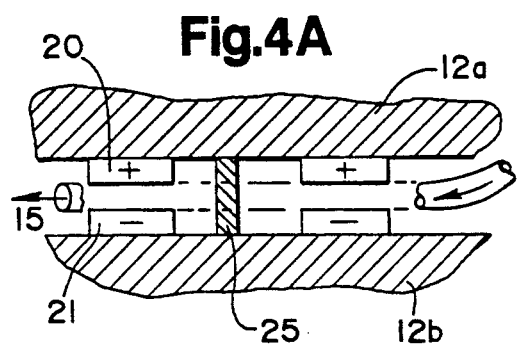
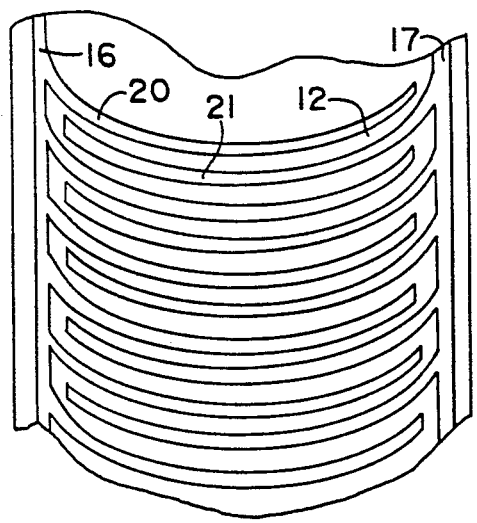
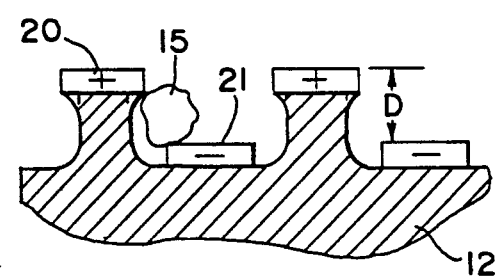

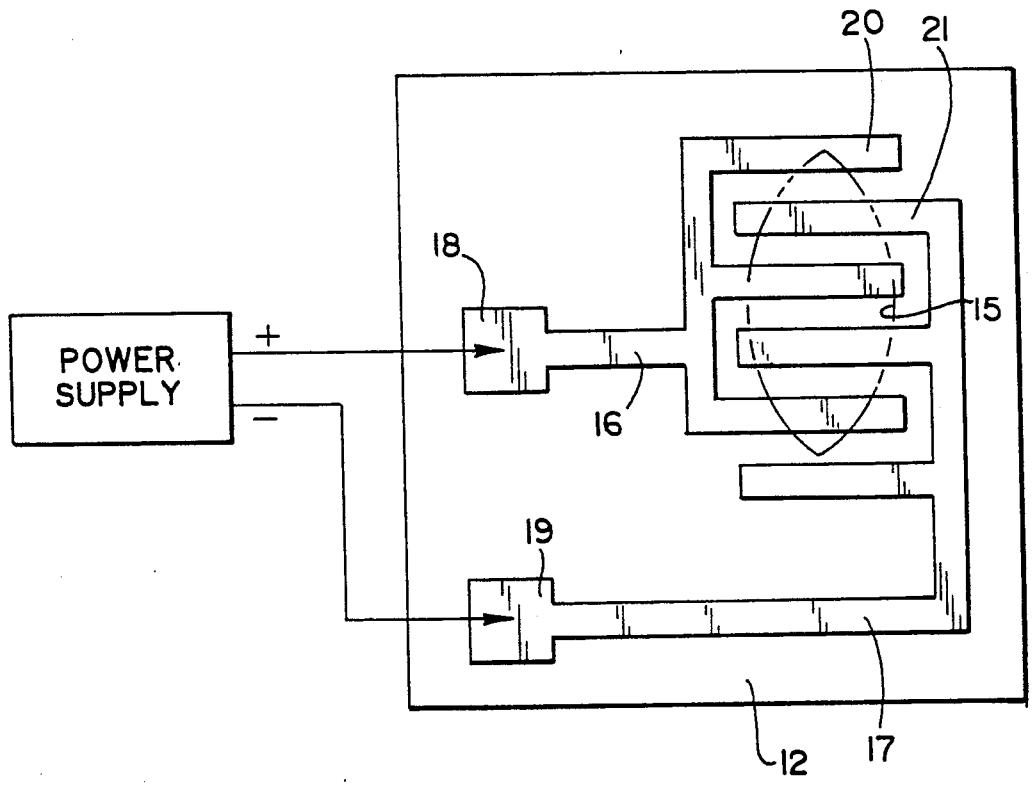

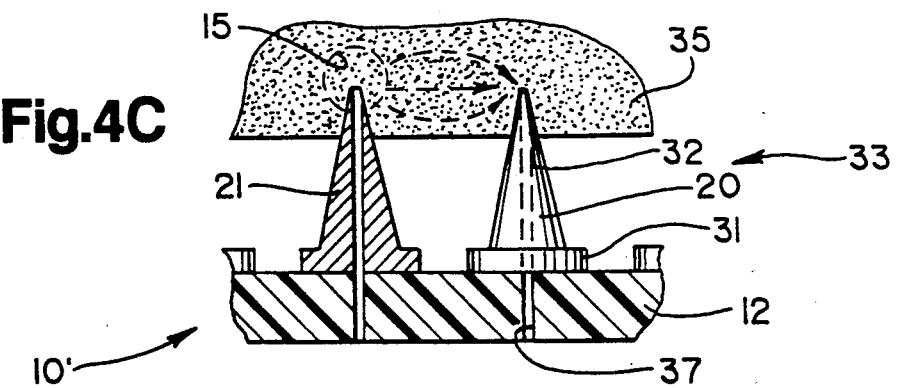
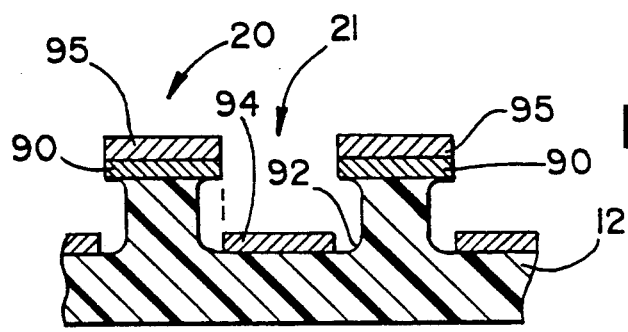
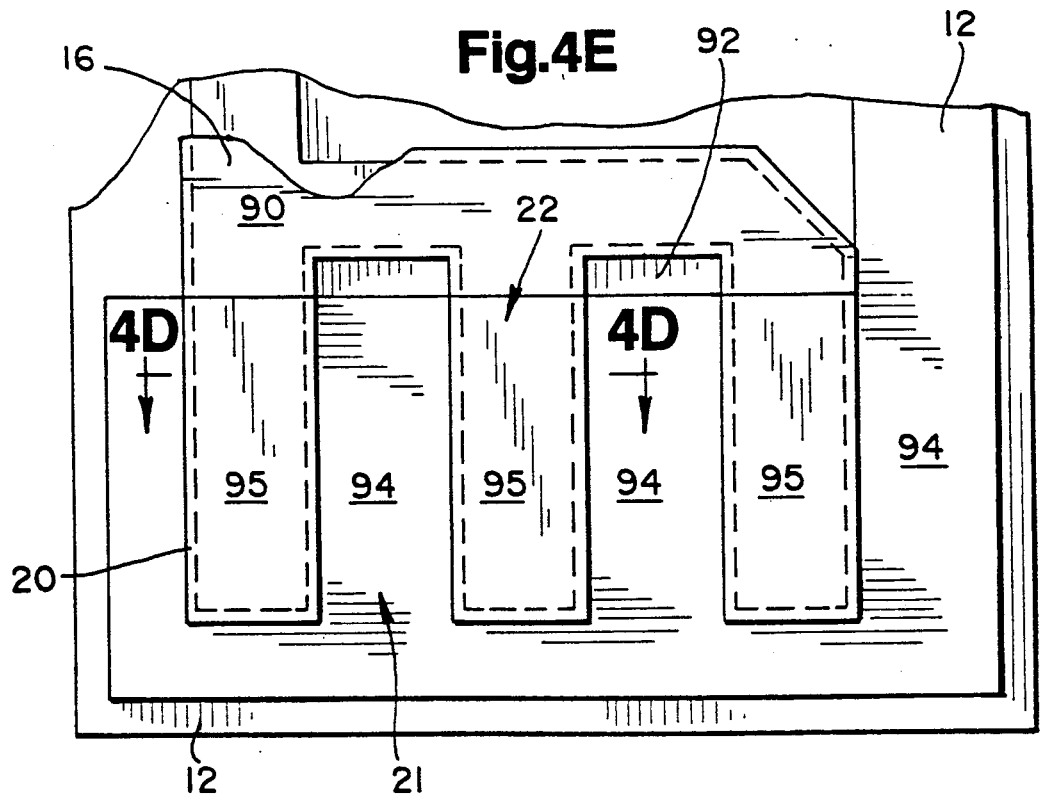

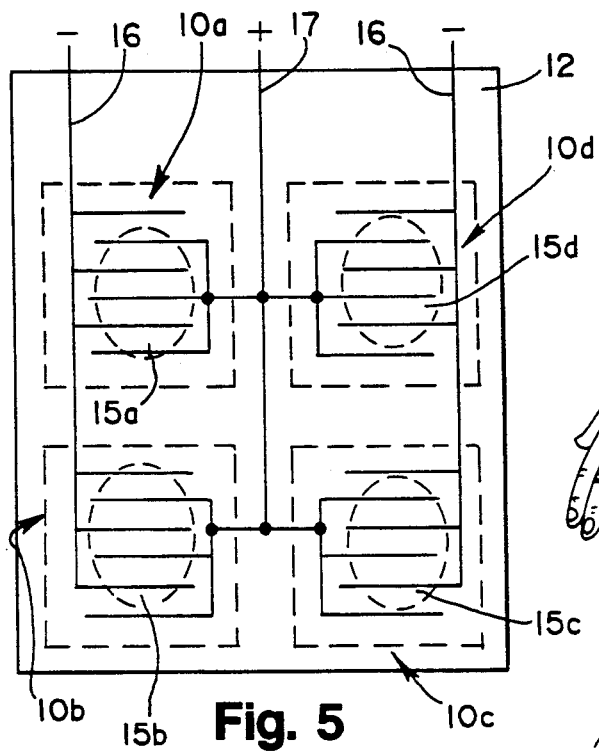
Fig. 5
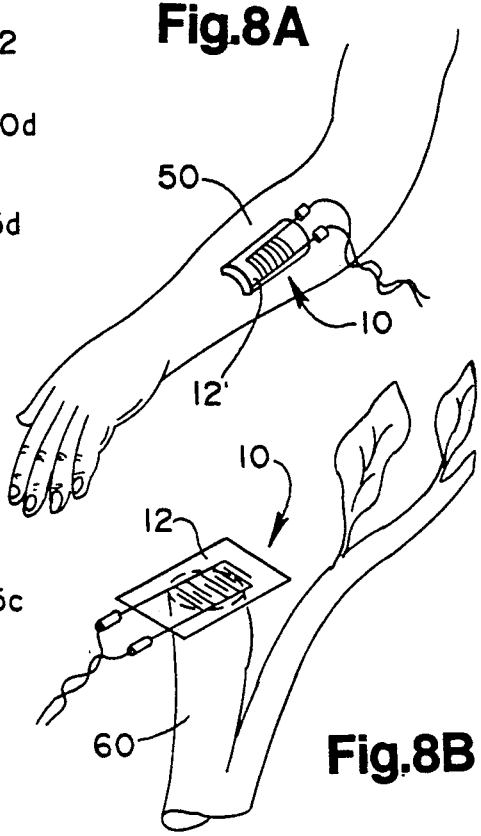
Fig. 8A
Fig. 8B
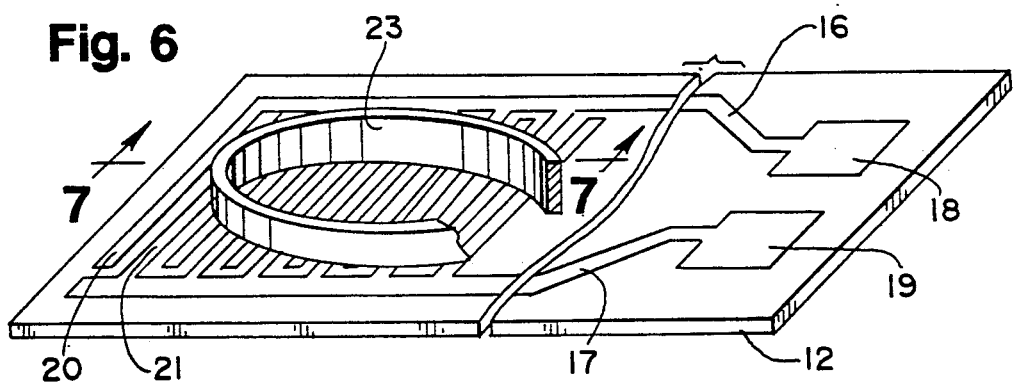
Fig. 6
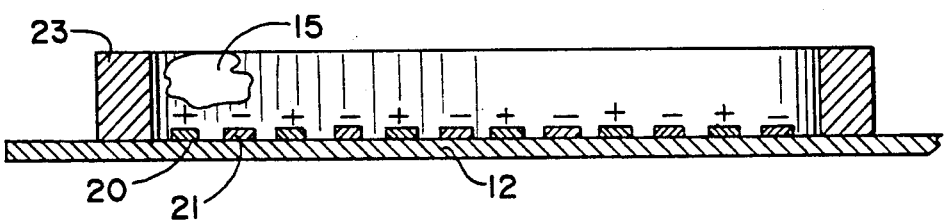
Fig. 7

APPARATUS AND METHOD FOR ELECTROPORATION

TECHNICAL FIELD

This invention relates to the general subject of electrotransformation of cells, and in particular to a method and apparatus for electroporation.

BACKGROUND OF THE INVENTION

The ability to manipulate the genetic content of living cells via transformation is one of the core technologies of the field of biotechnology. By altering the genetic repertoire of a cell, one can augment its normal capabilities, cause the cessation of some normal cellular activity or cause cells to perform activities which are entirely outside of their normal range of action. These possibilities have been exploited in many ways. Currently, the simplest and most common use of genetic manipulation is the reprogramming of cells to synthesize large amounts of desirable protein products. This kind of manipulation is usually performed on either unicellular organisms or on cells which have been abstracted from multicellular organisms and then maintained in culture as single cell types. As the number of available genes and the extent of knowledge about regulation of genes has expanded, greater and greater interest in altering the genetic constitution of normal multicellular organisms have been evoked. However, one of the primary limits to the alteration of multicellular organisms has been the technology available to carry out transformation.

The primary means for delivery of DNA into living cells are: cellular uptake of DNA precipitates, micro-injection of DNA into single cells, electro-fusion, insertion of DNA into cells by micro-projectiles coated with DNA, and cellular uptake of DNA from the surrounding solution following exposure of the cells to a strong electric pulse (i.e., electroporation or electro-transformation).

Cellular uptake of DNA precipitates requires that special non-physiological conditions be attained in the fluids surrounding the cells for relatively long periods of time (hour/s). This is not practical when dealing with whole multicellular organisms, as they have very effective systems which condition the fluids surrounding their cells.

Micro-injection of DNA into single cells is inefficient, tedious and very limiting in the number of cells which can be treated, since each treated cell must be individually handled.

Electro-fusion is a means by which exogeneous genetic material is introduced into a host plant (See U.S. Pat. No. 4,832,814 to Root). This insertion is accomplished by either permeabilizing the cell membrane to allow entry of genetic material or fusing the host cell with a cell containing the desired genetic material. Electro-fusion has many limitations and has not been found to apply to all plant cells. (See U.S. Pat. No. 4,822,470 to Chang).

Insertion of DNA into cells using DNA-coated micro-projectiles (See U.S. Pat. No. 4,945,050 to Sanford and Wolf) is another technology that has been used to genetically engineer plants. In one procedure the cells to be treated are exposed to a high vacuum, followed by a blast of gas and detritus from an explosive event. A vacuum is required so that the accelerated microprojectiles will retain sufficient velocity to pierce the target cells during their journey from the site of acceleration to the site of impact. The exposure to gas and debris from an explosive event arises from the need to use an explosion to achieve the high degree of acceleration required to give the micro-projectiles the requisite kinetic energy to pierce the target cells. Both of these conditions impose severe limitations to applying the projectile method to cells in whole organisms. This technology also requires that plants go through a tissue culture stage, and again the conditions for regenerating whole plants form plant cells are not well established for most plants. See D. E. McCabe, et. al., "Stable Transformation of Soybean (Glycine Max) by Particle Acceleration", BIO/TECHNOLOGY, Vol. 6, Aug. 1988, page 923; and J. C. Sanford, "The Biolistic Process", TIBTECH, Dec. 1988 (Vol. 6, page 299).

Cellular uptake of DNA following exposure of the cells to an electric pulse can take place in surroundings which are not too far from physiological, on time scales which are on the order of milliseconds. The current designs for devices to distribute the requisite electric pulses all utilize two electrodes whose surfaces are separated from each other by distances greater than 1 millimeter. H. Potter, "Electroporation in Biology: methods Applications, and Instrumentation", *Analytical Biochemistry*, 174, 361-373 (1988).

Furthermore, present day electroporation devices require that the target cells (i.e., the host cell and its transformant(s)) be placed into a cavity (e.g., a cuvette) formed between the electrodes. See U.S. Pat. No. 4,695,547 to Milliard et al; U.S. Pat. No. 4,764,473 to Matschke et al; U.S. Pat. No. 4,882,281 to Milliard et al; and the four U.S. Pat. Nos. 4,946,793; 4,906,576; 4,923,814; and 4,849,089 to Marshall. Such designs require that larger and larger voltages be applied to the plates with increasing cavity width to accomplish the same field strengths, and also place geometrical limits on what targets can be treated, by requiring that they be placed between electrodes. In fact, electro-transformation is routinely carried out on cells in suspension. If the cells were originally in a tissue, they are first dissociated to single cells or small aggregates of cells and then treated.

The conventional process and the equipment used in practicing electroporation also have practical drawbacks and shortcomings. Dangerous high voltages are required. Occasional arcing through bacterial suspensions can explode sample cuvettes and create bacterial aerosols. These kinds of technical problems require improvements in both power supply and sample cell design and performance. B. M. Chassy et al, "Transformation of Bacteria by Electroporation", TIBTECH, Dec. 1988 (Vol. 6, page 303).

In addition, attempts to insert new genes into cereal grains, such as corn, wheat and rice, have fallen short of total success. Researchers at the U.S. units of such companies as Ciba-Geigy Ltd. and Sandoz Corp., both Swiss owned, have inserted new genes into corn plants but the mature plants have been unable to reproduce. Smaller biotechnology companies like DNA Plant Technology Corp. In Cainnaminson, N.J., also are attempting to genetically alter corn. J. E. Bishop, "Scientists Report Inserting Gene into Corn Plants that Stay Fertile", *Wall Street Journal*, Technology & Science, Jan. 24, 1990.

One interesting application of electroporation has been the transformation of plant germplasm by introducing DNA into pollen and mating ova of a plant line with the transformed pollen (See U.S. patent application Ser. No. 350,356 filed on May 8, 1989 and assigned to U.S. Secretary of Agriculture). This procedure avoids the complications of regeneration from protoplasts or tissue culture. Still another means for breeding new plant varieties is to use microspores. Microspore culture is the technique of growing plants from immature pollen cells (See U.S. Pat. No. 4,840,906 ; to Hunter and European Patent 301,316 to E. Heberlebor et al).

Therefore, much remains to be done in the field of electroporation. Easier to use processes, inexpensive equipment and the ability to practice electroporation outside of the laboratory are improvements that would be welcomed by both the biotechnology industry and academic molecular biologists.

SUMMARY OF THE INVENTION

One object of the present invention is to provide an improved method and apparatus for carrying out electrotransformation of host cells by electroporation.

Another object of the present invention is to provide several unique arrays of interdigitated electrodes for transforming host cells by electroporation.

Yet another object of the present invention is to provide a versatile electroporation apparatus comprising an insulating substrate and a plurality of interdigitated electrodes formed from an electrically conductive film on the surface of the substrate.

Still another object of the present invention is to provide an electroporation apparatus comprising a flexible electrical insulating substrate which carries a plurality of electrodes in close proximity to each other.

Another object of the invention is to provide an apparatus and method for the electroporation of microspores.

Yet another object of the invention is to provide a method and apparatus which can be used to transform cells in vivo by electroporation.

In accordance with one aspect of the present invention, an apparatus is provided for transforming a host cell by electroporation. The apparatus comprises: at least one electrically insulating substrate; and at least two electrodes which are carried by said one substrate and which lie adjacent to each other, said electrodes and said substrate being adapted to be placed in close proximity to at least one cell transformant and at least one host cell, said electrodes and said host cell and said cell transformant being adapted to pass an electrical current therethrough upon the application of a potential difference across said electrodes, said electrodes having at least one of a difference in elevation relative to said one substrate, projecting means for physically penetrating at least a portion of a surface of an organisms carrying said host cells, and a difference in electrical conductivity.

One embodiment of the invention comprises: at least one electrically insulating substrate having a generally flat surface which is adapted to be placed adjacent to a host cell and its transformant which is separated from the host cell by a host cell membrane; and an interdigitated array of electrodes carried by the substrate, the electrodes comprise electrically conductive elements which are formed on the said flat surface of the substrate by depositing on the substrate an electrically conductive film and by subsequently removing preselected portions of the film.

In accordance with the method of the present invention, a process is described for electrotransformation of cells by electroporation comprising the steps of:

a) locating said cells in close proximity to an interdigitated array of electrode pairs which carry a cell transformant, adjacent electrodes of the array having at least one of a difference in elevation, means for physically penetrating at least a portion of a surface of an organism carrying the cells and a difference in electrical conductivity; and b) applying a potential difference to said electrodes to create a pulsed current flow between the electrodes.

The disclosed invention offers a faster and simpler method for transforming cells. Compared with the cost of laborous search for a natural transformation system and the inherent difficulties of the biolistic process, it offers an improved means by which a wide variety of cell hosts can be transformed.

Moreover, almost any biological surface which can be placed in contact with the electrodes can be treated. The invention allows one to obtain not only the usual benefits of rapid treatment time and the nearly physiological conditions provided by electro-transformation, but also the benefits of lower applied voltage requirements and easy access to cells on readily exposed tissue surfaces. The combination of these features permits topographically targeted transformation of regions of living organisms. For instance, animal dermal cells can be transformed by a procedure which is minimally invasive. As the skin as well vascularized, transformation of the dermis with genes which produce secreted products results in the systematic delivery of these products. This approach has interesting applications to vaccination, to diseases where accumulation of noxious substances in the blood stream is problematic and to pathologies involving deficiencies in normally circulating products. Another example of a use of the invention is the transformation of microspores and meristematic plant cells exposed by wounding (e.g., exposing) a growing plant stem. Such a transformed cell has a good chance of proliferating and eventually becoming (e.g., leading to) a germ cell, which would allow production of a totally transgenic plant.

Numerous other advantages and features of the present invention will become readily apparent from the following detailed description of the invention, the embodiments described therein, from the claims, and from the accompanying drawings.

BRIEF DESCRIPTION OF THE DRAWINGS

FIGS. 1 and 3C are plan views of two embodiments of electrode sets that are the subject of the present invention;

FIG. 2 is an enlarged, partial plan view of the electrode set of FIG. 1;

FIGS. 3A and 3B are enlarged, partial plan views of alternative interdigitated electrode arrays.

FIGS. 4A and 4B are partial, side cross sectional schematic representations of two interdigitated arrays wherein the electrodes are not located in a single flat plane;

FIG. 4C is a partial, side, cross sectional schematic representation of an electrode array which has pointed ends;

FIG. 4D is a partial, side, cross sectional view which illustrates one means by which the electrode set of FIG. 4B can be formed;

FIG. 4E is a partial plan view of the array of FIG. 4D when completed;

FIG. 5 is a plan view of a plurality of electrode arrays located on a common substrate;

FIG. 6 is a perspective view of a substrate which carries an electrode array showing a cut away view of a retention means for carrying a cell host and/or transformant;

FIG. 7 is a cross sectional, side view of the apparatus of FIG. 6; and

FIGS. 8A and 8B are perspective views of electrode arrays on a flexible substrate and in close proximity to a living cell host.

DETAILED DESCRIPTION OF PREFERRED EMBODIMENTS OF THE INVENTION

Figure 4F:
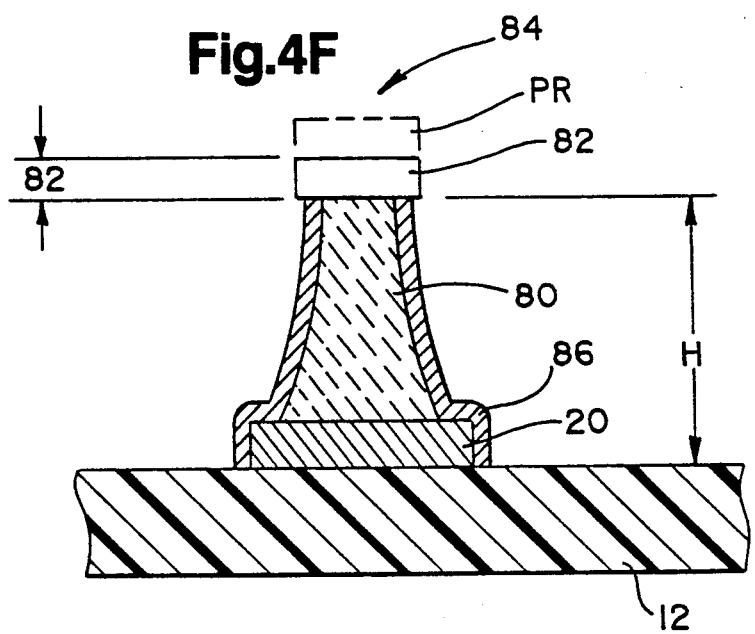
FIGS. 4F and 4G are partial, cross sectional side and perspective views of an electrode array having a plurality of skin or tissue penetrating protrusions.

While this invention is susceptible of embodiment in many different forms, there is shown in the drawings and will herein be described in detail several specific embodiments of the invention. It should be understood, however, that the present disclosure is to be considered an exemplification of the principles of the invention and is not intended to limit the invention to any illustrated specific embodiment.

Turning to FIG. 1, there is illustrated a basic embodiment of the present invention. Specifically, a microporator 10 is illustrated. The microporator 10 is an electroporation device which comprises an electrically insulating substrate 12, a plurality of interdigitated electrodes pairs or sets 14 which form a generally flat planar electrode array, common bus bars 16 and 17 for electrodes of the same or common polarity, and a pair of input terminals 18 and 19 for the bus bars. The input terminals are connected to a pulsed power supply. The cell host and a transformant 15 are positioned on the underlying substrate and electrode array.

For convenience, the same substrate 12 can be used to form a plurality of individual electrode sets 10, 10b and 10c. After formation, the substrate 12 can be cut (see broken lines 13) to form individual electrode sets. By choosing a substrate which is flexible and rollable a plurality of electrode arrays can be formed on the same substrate and dispensed serially.

FIG. 2 illustrates details of the interdigitated electrode array 14 of FIG. 1. Specifically, the array 14 comprises a plurality of electrode pairs 20 and 21 which extend at right angles from the two bus bars 16 and 17 and which are adapted to be be connected to the positive (+) and negative (−) terminals of a DC power supply or source, for example. The electrodes are parallel to each other and lie on the top surface of the underlying electrically insulating substrate 12.

In one particular embodiment, the substrate 12 was formed from a 2 inch diameter soda-lime glass of 0.060 inches thickness. A 100 nm thick NiCr film was deposited by e-beam evaporation on top of the substrate 12 and was photoshaped to define the interdigitated electrode array 14. The film can also be deposited by chemical vapor deposition, sputtering, and plating. More specifically, after NiCr film is deposited, a 1 $\mu$m layer of photoresist (e.g. Shipley 1470) was spun on, baked and exposed with UV light through a mask which defines the interdigitated pattern of the microporator 10. The line width of the NiCr electrode elements was chosen as 12 micrometers with 100 micrometers spacing between individual electrode elements. Fifteen electrode pairs 14 were defined by the mask. The photoresist was developed (i.e., washed away) in the exposed areas, leaving an interdigitated pattern or array on the NiCr film. Afterwards, the NiCr was etched chemically (e.g., GFS etchant) in the areas not protected by the photo-resist. Finally, the photo-resist on top of the remaining NiCr was stripped.

To optimize the electrode set 10 for different host cell geometries, the width (e.g., 0.5 $\mu$m to 1000 $\mu$m) and spacing (e.g., 1 $\mu$m to 1000 $\mu$m) of the electrode pairs 20 and 21 can be adjusted. Close spacing of the electrodes 20 and 21 in an array 14 allows development of strong electric fields in the vicinity of the electrodes with lower applied voltages than a conventional system. Care should be taken not to make the bus bars 16 and 17 so narrow that they act like a fuse element when the DC voltage is applied. Increasing the film thickness (e.g., 200 nm, 300 nm, etc) or changing the metal can help. It will become apparent from the discussion which follows that the physical arrangement just described has great versatility in application of electroporation.

We have found that when the electrodes 20 and 21 are made from the same material, electrolytic decomposition occurs. Specifically, if the electrodes are all made of the same metal, then the electrodes connected to the positive terminal (+) of the power supply undergo oxidation and deterioration. If the electrodes are all made of an oxide of a metal, then the electrodes connected to the negative terminal (−) of the power supply undergo reduction and deterioration. In some cases, the array became unusable after one poration cycle. For long use, one set of electrodes are preferably made from a metal and the other set of electrodes are made from an electrically conducting metal oxide and connected to the positive terminal.

GENERAL PROCEDURE

The microporator set 10 may be used in accordance with conventional electroporation techniques. For example, host cells are cultured, harvested, washed free of media components and resuspended in water, or a low conductivity buffer. The resuspension solution might contain an osmotic stabilizer, most often sucrose. Next, an aliquot of host cells is placed on ice and chilled for ten minutes. DNA, the host cell transformant, is added, and the cells are immediately placed in contact with the electrode set 10 to which a DC voltage pulse is delivered. The voltage and capacitance are set on the power supply. An auxiliary resistance network may be interposed between the power supply and the input terminals 18 and 19 of the electrode set 10. The time constant may be varied independently of the voltage. Immediately after the power pulse is applied, the host cells are removed from the electrode set and are diluted into a growth medium. In some cases, transformed cells may be plated directly on selective media, while in other cases it is necessary to incubate the cells for one to four hours in the growth medium prior to plating in order to obtain good transformation efficiency or frequency.

SPECIFIC EXAMPLE

The apparatus of the present invention has been successfully used to transform bacterial cells using the following protocol:

Host Cell Preparation

*E. coli* cells (strain JM101) from a single bacterial colony were cultured at 37° C. in 100 ml of Luria Broth (1% Bacto-Tryptone, 0.5% Bacto Yeast Extract, 0.5% NaCl) contained in a 1 liter flask until the culture reached an optical density of 1, when measured at 590 nm. The culture was then transferred to an ice water bath for 15 minutes. Cells were harvested by centrifugation at 4000xg, at 4° C. for 5 minutes. The cells were then resuspended in 100 ml of 1 mM Hepes (pH 7) buffer (4° C.) and recovered by centrifugation (as before). The cells were resuspended in 10 ml of 20% glycerol in water (40° C.) and recovered by centrifugation (as before). Thereafter, the cells were resuspended in 2 ml of 20% glycerol in water (4° C.). The final suspension of cells was divided into 50 µl aliquots in Nalgene Cryo-Vials and was frozen by immersing the vials in liquid nitrogen. The frozen vials were stored at −80° C. until use. The number of cells in the final suspension was determined to be $2 \times 10^{10}$ by counting a 1/100 dilution of the suspension in a Hausser Counting Chamber.

Electrode Array

The electrodes of the array comprised thirty 100 nm thick, 12 nm wide, 1 cm long, NiCr film strips which were separated from each other by 100 µm and fomed a 0.3 by 0.3 cm array (See FIG. 2).

Transforming DNA

The DNA used for this experiment was the plasmid pUC19. It was prepared by standard methods. The DNA concentration of the stock solution of DNA was 150 µg/ml.

Transformation Procedure

The frozen cell suspension was thawed rapidly by immersion in a 37° C. bath and then held at 0° C. on ice until use. The treatment regime was to spot a 4µl aliquot of the cells onto the electrode array 10 and to subject the cell suspension to a pulse generated by a Bio-Rad Gene Pulser/Pulse Control Unit. The Bio-Rad Gene Pulser is a capacitor discharge device that is totally self-contained; a continuously variable range of voltage from 0 to 2 kV, and four capacitances (0.25, 1.0, 3.0, and 25 µF) are provided. A 2 µl sample of the cell suspension was then removed and inoculated into 1 of SOC culture media (2% Bacto Tryptone, 0.5% Bacto Yeast Extract, 10 mM NaCl, 2.5 mM KCl, 10 mM MgCl$_2$, 10 mM MgSO$_4$, and 20 mM glucose). The array was then rinsed with 3 washes of 1 mM Hepes (pH 7) buffer to prepare it for the next treatment cycle.

The treated host cells were allowed to recover in SOC media for 1 hour at 37° C. The cells were then recovered by centrifugation at 5000 xg for 2 minutes and spread onto LB/Amp agar plates (1% Bacto-Tryptone, 0.5% Bacto Yeast Extract, 0.5% NaCl, 1.8% Bacto Agar 200 µg/ml ampicillin). Cells spread onto these plates were allowed to incubate at 37° C. overnight. An unaltered *E. coli* strain JM101 is unable to grow in the presence of the drug ampicillin at the concentrations used in the electrotransformation procedure or process just described; however, *E. coli* strain JM101 which contains the plasmid pUC19 is capable of growth in the presence of 200 µg/ml ampicillin. Thus, growth of cells which took up the plasmid, results in the production of a colony, allowing evaluation of the efficiency of plasmid uptake.

Results

The results of various control and experimental treatments of the cells is presented in the table below.

| Treatment Gene Pulser Settings | | uls of: | | Result: Colonies |
|---|---|---|---|---|
| Volts | Capacitance | cell suspension | DNA | Observed |
| 50  | 25 µF | 4 | 0     | 0 |
| 70  | 25 µF | 4 | 0.025 | 0 |
| 100 | 25 µF | 4 | 0.025 | 0 |
| 200 | 25 µF | 4 | 0.025 | 850 |
| 500 | 25 µF | 4 | 0.025 | >5000 |

It is clear that cell transformation was produced by some of the applied pulses. Since bacteria are hard to transform relative to cells from eukaryotes (i.e., susceptibility is though to be related to cell size), transformation of eukaryotes should be readily achieved by the method and apparatus of the present invention.

This series of trials demonstrated the usual guideline that a range of parameters should be evaluated to determine the optimum combination for each cell transformation of interest. This is not difficult experimentally. The choice of time constant is usually restricted by power supply capacity as well as by the conductivity of the electoportation medium. Decay times of the discharge of 2.5 to 10 msec duration are often effective. Changes in buffer ions, pH, conductivity, dielectric constant and buffer concentration may effect the time constant as well as the transformation efficiency or frequency. A variety of electroporation buffers should be also be considered. Total failures are not unexpected. The basis for these differences is complex and not completely understood by those skilled in the art. For example, failure may stem from: (1) choice of the cell transformant or the DNA, (2) host restriction barriers, (3) the non-replication of plasmids, or (4) the non-expression of a marker gene; it is usually difficult to determine the exact cause.

SECOND EXPERIMENT

Here the object was to observe the operation of the electrode set 10 to introduce active genes into plant cells, both to equate the invention with existing technology and to see if the invention could be used to stably transform whole plant cells (carrots). In particular the "CAT" genes (chloramphenicol acetyl transferase), under the control of a plant-active promoter (e.g., a cauliflower mosaic virus promoter), were used to determine if the genes could enter the plant cell and be expressed. Protoplasts (carrot cells with their walls enzymatically removed) were treated with CAT and without CAT (i.e., Control). The electrode set was used with 4V, 20V, and 200V at 1000 µF. A CAT assay (i.e., a tie TLC analysis of the reaction) showed the formation of:

1' acetylchloramphenical;
3' acetylchloramphenical; and
1'-3' acetylchloramphenical.

This clearly showed that CAT gene transfer had been achieved.

THIRD EXPERIMENT

Maize microspores (immature pollen at uninucleate to binucleate stage) were prepared for electroporation and subjected to 2 volts, 505 microfarad electrical pulses using the apparatus of FIG. 1. The transformation of the microspores with added DNA plasmids was assayed by measuring the chloramphenicol acetyl transferase activity imparted by CAT genes driven by either alcohol dehydrogenase-Intron 1, or ubiquitin promoters. No activity was detected in treated cells without added CAT genes.

More specifically, the transformant was selected for use with 500 μl of microspores using DNA at a concentration of 20 μg/ml. The constructs were pADH-intron 1-CAT and pVbiq-CAT. The microspores (genotype H99XPa91) were prepared by collecting tassels (in the uninucleate to binucleate stage) and cold treating them at 8° C. for two weeks. Next, the tassel florets were surface sterilized using 70% ETOH for 60 sec., followed by a 10% bleach+Tween-20 solution for 12 minutes and three sterile water rinses. Afterwards, the florets were homogenized in 4° C. sterile water sucrose for 30 to 60 seconds and any debris was removed by filtration. The slurry was then centrifuged in Babcock bottles at 950 rpm for 10 minutes. Finally the microspores were collected and counted. A yield of $13.2 \times 10^6$ microspores/ml ($3 \times 10^6$ when diluted in HBS) was observed.

Four situations were studied using 5 batches of 100 μl of microspore for each situation:

|     | Voltage | Capacitance | Transformant     |
| --- | ------- | ----------- | ---------------- |
| I   | 2 v     | 505 μf      | pADH-intron 1-CAT |
| II  | 2 v     | 505 μf      | pUbiq-CAT        |
| III | 2 v     | 505 μf      | pUbiq-CAT        |
| IV  | 2 v     | 505 μf      | NONE (control)   |

A CAT assay was performed using a Thin Layer Chromogram. No activity was detected in the treated cells without the added CAT genes (i.e., CAT activity was observed for situations I, II, and III).

FOURTH EXPERIMENT

Three electrode spacings were tested with 250 VDC and 25 μF and the current flow through the electrodes, the host cells (*E. coli*) and the cell transformant was observed:

| Electrode Separation | Max Current |
| -------------------- | ----------- |
| 5 μm                 | 2.2 Amps    |
| 30 μm                | 1.5 Amps    |
| 100 μm               | 0.5 Amps    |

In each case the electrodes were 100 nm thick. The most transformation occurred when the electrodes were spearated by 100 μm. Further efficiency may be achieved by varying electrode spacings and applied voltages.

Turning to FIGS. 3A, 3B and 3C, three additional interdigitated electrode arrays are illustrated. In FIG. 3A, each adjacent electrode 20 and 21 is formed from a plurality of broken line segments or elements. in FIG. 3B, the adjacent electrodes are formed from parallel arcuate segments. In FIG. 3C, each electrode 20 and 21 is located parallel to the two bus bars 16 and 17. Other variations should be readily apparent to those skilled in the art.

Heretofore the electrodes 20 and 21 of the array 14 were shown generally lying in the same plane (e.g., atop a flat surface of the substrate 12), in FIGS. 4A and 4B, the electrodes of the array lie in two parallel planes. One advantage of a non-planar array is that adjacent electrodes 20 and 21 can be brought close to each other (i.e., micron and submicron vertical separation at "D"). In particular, by adjusting the elevation of the electrodes relative to the cell 15 undergoing transformation, excess stress on the cell walls may be avoided and cell survival enhanced.

Turning to FIG. 4A, one substrate 12a carries electrodes 20 of one polarity (e.g., positive) and another substrate 12b carries electrodes 21 of the opposite polarity. Alternatively, electrodes of one polarity can be located on one substrate and electrodes of the opposite polarity located on an adjacent similar substrate. A spacer 25 may be used to maintain the required separation. In FIG. 4B, the electrodes 20 and 21 lie in two different planes and share a common substrate.

The structure of FIG. 4A can be obtained by methods similar to that used to form the substrate and electrodes of FIG. 1. The structure 12 of FIG. 4B can be formed in a number of ways. For example, turning to FIG. 4D, after a metal film 90 has been deposited on the substrate and after the film which is not protected by the photo-resist has been etched away, the etching of the substrate is continued to dissolve the exposed substrate 12 to the desired depth 92 to achieve the required final separation "D" allowing for any the thickness of the electrodes. Thereafter, the remaining photo-resist is stripped away to expose the metal base 90 for one set of electrodes 20.

Next, a second electrically conductive film 94 is deposited; a layer of photo-resist is applied, is exposed with UV light through a second mask which defines the other electrodes 21 and their connection to the bus bar and is washed away. Afterwards, the second metal 94 is etched away in the areas 95 not protected by the photo-resist. Finally, the remaining protective photo-resist is removed (See FIG. 4E).

FIG. 4C illustrates a microporator 10 having pointed electrodes 20 and 21. Specifically, each electrode has a flat end or base 31 which is located adjacent to the substrate 12 and has an opposite skin penetrating end or projection 32. A cell transformant 15 can be carried by or located on or injected through the pointed end 32 (using passageways 37), whereby, upon puncturing the envelope (e.g., inactive surface tissue or dead skin layer 33) of the active layer 35 of the living organism which comprises the host cells, the electrodes 20 and 21 come into contact with the host cells. After penetration the electrodes would be energized.

Figure 4G:
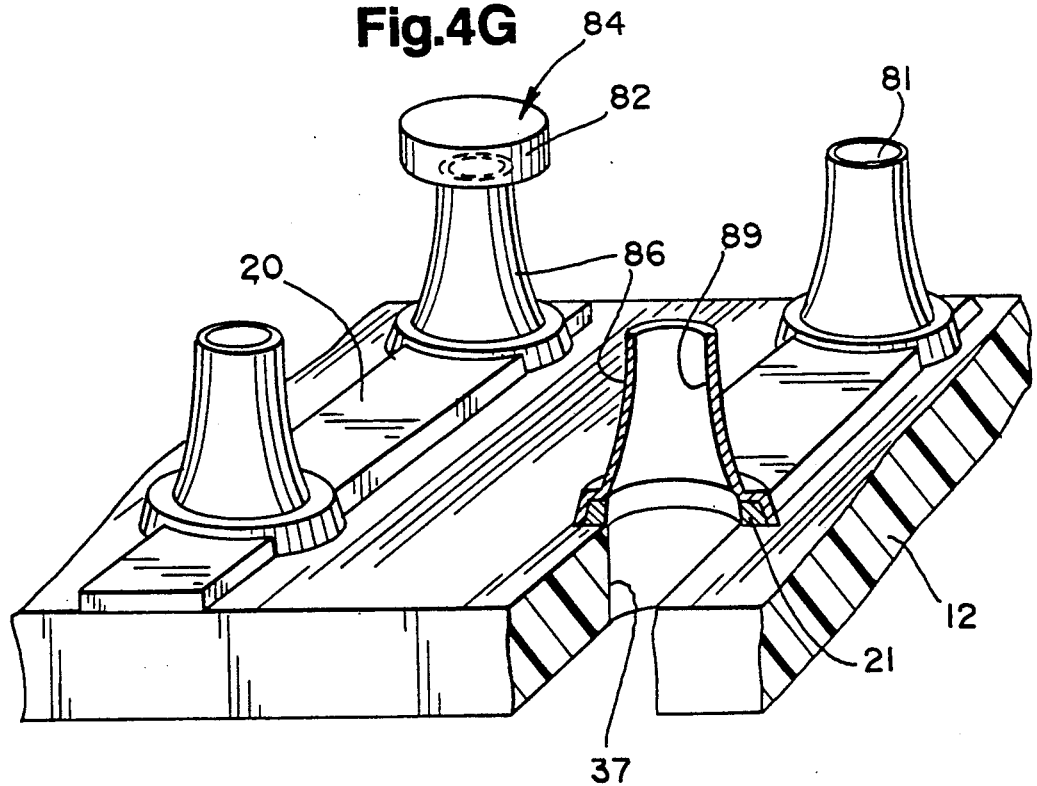

There are several techniques which can be used to form the electrodes of FIG. 4C. For example, turning to FIG. 4F, after a conductive film or layer (e.g., Pt, Ni, W, Ti, Mb, $MoSi_2$, etc.) has been deposited on the substrate 12 and the film which is not protected by the photo-resist has been etched away to form the flat side or base of electrodes 21 and 22, and after the remaining photo-resist is removed, a layer 80 of polycrystalline silicon is deposited on the electrodes 20 and 21 to a depth of several microns. Next, the surface of the silicon is oxidized 82 to a thickness of about 100 to 300 n. Thereafter, a mask is used to define the plan form of individual protrusions (e.g., square, circular, etc.) on the $SiO_2$ layer 82 using the photo-resist method much as that previously described. Next, the unprotected silicon dioxide is etched leaving an array of "islands" 84 (about 2 to 10 μm in diameter and spaced about 10 to 100 μm apart) on the electrodes 20 and 21. Anisotropic or isotropic etching is used next to etch the polycrystalline silicon layer 80. Then, an electrically conductive layer 86 is deposited (e.g., by boron diffusion, or by using the silicon or hydrogen reduction of WF$_6$) on the silicon 80 and on the base metal of the electrodes 20 or 21 (See FIG. 4G). Finally, the top of the elevated islands 84 can be etched away to form channels 89 or DNA reservoirs 81 (FIG. 4G). The interior of the conductive layer 86 and the film 20 and 21 serves as an etch stop for etching the silicon 80. Internal passage ways 37 (See Fig. 4C) can be formed by etching the substrate 12 and portions the of electrodes 20 and 21 from the opposite side. The overall height "H" is about 30 $\mu$m (e.g., about 1 to 40 $\mu$m, depending on the application).

Turning to FIG. 5 there is illustrated a microporator set comprising a plurality sets of interdigitated electrodes arrays 10a through 10d, all carried on a common substrate 12. The individual arrays can be arranged in any suitable pattern (i.e. circular, radial, etc.). Here a rectangular pattern of four individual arrays is illustrated. Such an arrangement allows multiple biological specimens 15a through 15d to be eletrotransformed simultaneously.

In FIG. 6 and 7, an arrangement is shown wherein the planar array of FIG. 1 is provided with a damming means 23, (i.e., a well, retention or fluid confining element) to properly locate the biological species or transformants 15 relative to the interdigitated elements 20 and 21 of the electrode array. This well 23 can be formed by photoresistance techniques. A well 23 integrated with the electrode set is preferred.

The electrical insulating substrate 12 need not be rigid. Electrode sets 10 can also be fabricated on flexible substrates, such as kapton. One advantage of a flexible electrode set is that the electrode array can be bent to conform to the contours of the living organisms which carries the host cells. (See FIG. 8A and 8B) For example, host liver cells of a mouse can be transformed by using pRSVCAT which is carried by an electrode set which is located in close proximity with the host cell. In FIG. 8A an electrode array 10 with a flexible substrate 12' is applied to the arm 50 of a human. FIG. 8B illustrates an electrode array 10 located atop the stem 60 of a plant.

The complete electrode set 10 can also be made disposable. Such a feature would allow multiple cell hosts to be transformed at low cost and without having to clean and sterilize the electrodes after each use. Disposability is a particularly practical advantage of the invention inasmuch as the electrode sets can be made in large quantity at low cost. The technology used in the production of the circuit boards can really be applied to the invention. Conveniently, a plurality of electrode sets (See FIG. 1) can be formed serially on a flexible, rollable and disposable substrate. If desired, the disposable portion, which contains the electrode array 14, can be dropped into the culture medium after the pulsing operation is completed. Of course, if the cells were originally in a tissue, they are first dissociated to single cells or small aggregates of cells and then treated. A new, sterilized electrode set 10 can be joined to the power supply (via a reusable electrical connection or plug set) and a new experiment can be performed.

From the foregoing description, it will be observed that numerous variations, alternatives and modifications will be apparent to those skilled in the art. Accordingly, this description is to be construed as illustrative only and is for the purpose of teaching those skilled in the art the manner of carrying out the invention. Various changes can be made and specific features of the invention can be modified. For example, there is no practical limit on the area of the array provided the current/electrical field is adequate to achieve transformation. Similarly, the electrodes can be arranged in a star shaped pattern wherein the electrodes are not parallel to each other or in a continuous interwoven pattern. The invention enables the user to perform electro-transformations along a surface and over a specifiable large or small area. Materials may be substituted and particular features of the invention may be utilized independently of the other. For example, a tube or channel can be formed between the electrodes (See FIG. 4A) of the array for the flow (e.g., using a micropump) of the cell host and its transformant, whereby continuous electroporation can be conducted. Similarly, the pointed electrodes 20 and 21 of FIG. 4C can be provided with an internal channel 37 for delivering transforming cells 15 to the host cells 35 after the pointed ends have passed through the dead or inactive envelope 33 which surrounds the targeted host cells. This is more efficient then preapplying the cell transformants to the electrodes before penetration. Moreover, the apparatus of the present invention may be used for transformation of embryo, embroyogenic callus tissue and meristemic regions (both leaf and bud) and other means by which a tissue culture stage is obviated. Thus, it will be appreciated that various modifications, alternatives, variations, etc., may be made without departing from the spirit and scope of the invention as defined in the appended claims. It is, of course, intended to cover by the appended claims all such modifications involved within the scope of the claims.

We claim:

1. An apparatus for transforming of a host cell by electroporation, comprising: at least one electrically insulating substrate; and at least two electrodes which are carried by said substrate and which lie adjacent to each other, said electrodes and said substrate being adapted to be placed in close proximity to at least one cell transformant and at least one host cell, said electrodes and said host cell and said cell transformant being adapted to pass an electrical current therethrough upon the application of a potential difference across said electrodes, said electrodes having at least one of a difference in elevation relative to said substrate, projecting means for physically penetrating at least a portion of a surface of an organism carrying said host cells, and a difference in electrical conductivity.

2. The apparatus of claim 1, wherein said electrodes and said substrate have upper surfaces, said upper surface of one electrode having a greater elevation relative to said upper surface of said substrate than said upper surface of the adjacent electrode, whereby at least two of said electrodes have an difference in elevation.

3. The apparatus of claim 1, wherein one electrode is formed from a metal and an adjacent electrode is formed from an oxide of said metal, whereby said adjacent electrodes have a difference in electrical conductivity.

4. The apparatus of claim 1, wherein said electrodes and said substrate have upper surfaces, said upper surface of one electrode having a greater elevation relative to said upper surface of said substrate than said upper surface of an adjacent electrode, whereby said adjacent electrodes have a difference in elevation and a difference in electrical conductivity.

5. The apparatus set of claim 1, wherein said substrate comprises generally flexible electrical insulating base.

6. The apparatus of claim 1, wherein at least one electrode carries projecting means for physically penetrating at least a portion of the surface of an organism comprising said host cells.

7. The apparatus of claim 6, wherein said substrate has a generally flat face and said one end of said one electrode has two opposite generally flat sides, one of said sides being carried by said one flat face of said substrate and the opposite side carrying said projecting means.

8. The apparatus of claim 6, wherein said projecting means is adapted to carry said cell transformant.

9. The apparatus set of claim 1, wherein said electrodes are generally flat and generally parallel to each other; and wherein said electrodes were formed on said substrate using a film depositing process selected from the group: sputtering, e-beam evaporation, diffusion and plating.

10. The apparatus claim 1, wherein said substrate carries a plurality of interdigitated electrodes which form said array.

11. The apparatus of claim 10, wherein said substrate is generally flexible and rollable.

12. The apparatus of claim 1, wherein said electrodes comprise a plurality of electrode pairs; and wherein said plurality of electrode pairs are carried by a common electrically insulating substrate.

13. The apparatus of claim 12, wherein said electrode pairs are adapted to be connected to a common power supply for applying said potential difference.

14. The array of claim 1, wherein said host cell is a microspore.

15. The array of claim 10, wherein said electrodes are separated by at least 1 $\mu$m and less than 1000 $\mu$m.

* * * * *

UNITED STATES PATENT AND TRADEMARK OFFICE
CERTIFICATE OF CORRECTION

PATENT NO. : 5,137,817
DATED : August 11, 1992
INVENTOR(S) : Heinz H. Busta, et al It is certified that error appears in the above-indentified patent and that said Letters Patent is hereby corrected as shown below:

Col. 1, line 10, "plants form plant" should read --plants from plant--

Column 9, line 55 reads "were spearated" and should read --were separated--
Column 10, line 61 reads "100 to 300n" and should read --100 to 300 nm--

Signed and Sealed this

Fifth Day of July, 1994

Attest:

BRUCE LEHMAN

*Attesting Officer*  *Commissioner of Patents and Trademarks*